US009433785B2

(12) United States Patent
Holding et al.

(10) Patent No.: US 9,433,785 B2
(45) Date of Patent: Sep. 6, 2016

(54) HEALING DISC, A PAIN MANAGEMENT ASSEMBLY INCORPORATING THE DISC, AND A METHOD OF USING THE SAME

(71) Applicant: Garth Howard Holding, Durham (CA)

(72) Inventors: Garth Howard Holding, Durham (CA); Robert G. Dickie, King City (CA)

(73) Assignee: Garth Howard Holding, Durham, Ontario (CA)

( * ) Notice: Subject to any disclaimer, the term of this patent is extended or adjusted under 35 U.S.C. 154(b) by 67 days.

(21) Appl. No.: 14/058,405

(22) Filed: Oct. 21, 2013

(65) Prior Publication Data
US 2015/0112404 A1    Apr. 23, 2015

(51) Int. Cl.
*A61N 1/04* (2006.01)
*A61N 1/37* (2006.01)
*A61N 1/36* (2006.01)
*A61N 1/32* (2006.01)

(52) U.S. Cl.
CPC ......... *A61N 1/36021* (2013.01); *A61N 1/0456* (2013.01); *A61N 1/0492* (2013.01); *A61N 1/326* (2013.01)

(58) Field of Classification Search
CPC .......................... A61N 1/0456; A61N 1/3756
See application file for complete search history.

(56) References Cited

U.S. PATENT DOCUMENTS

| | | | |
|---|---|---|---|
| 4,989,605 A * | 2/1991 | Rossen | 607/46 |
| 5,387,231 A * | 2/1995 | Sporer | A61N 1/36021 607/48 |
| 6,567,695 B1 | 5/2003 | Gruzdowich et al. | |
| 6,567,702 B1 * | 5/2003 | Nekhendzy | A61N 1/36025 607/139 |
| 7,922,676 B2 | 4/2011 | Daskal et al. | |
| 2007/0167992 A1 * | 7/2007 | Carley | 607/46 |
| 2010/0217349 A1 * | 8/2010 | Fahey | 607/48 |
| 2013/0158627 A1 * | 6/2013 | Gozani et al. | 607/46 |
| 2013/0245712 A1 | 9/2013 | Simon et al. | |
| 2014/0148872 A1 * | 5/2014 | Goldwasser et al. | 607/45 |

OTHER PUBLICATIONS http://mywellcare.ca/tens_units/ev-807p_digital_tens_ems_n.m.e.s., 2 pages, document is undated but publicly available as of Nov. 13, 2013.

* cited by examiner

*Primary Examiner* — Edward Moran
*Assistant Examiner* — Natasha Patel
(74) *Attorney, Agent, or Firm* — Sand & Sebolt

(57) ABSTRACT

A portable, wearable device for managing pain and promoting healing, a management assembly including such a device, and a method of using the same. The device includes a housing defining a cavity; a microprocessor situated within the cavity; a power source operatively connected with the microprocessor; and a pair of electrodes. The electrodes are mounted in apertures in a bottom wall of the housing and extend for a distance there beyond. One or more mounting assemblies are used with the device to provide a management assembly. The mounting assembly may be a strap having a retaining ring into which the device fits, or an adhesive patch configured to receive the device. The device is engaged with the mounting assembly and then positioned adjacent the patient's skin. When activated, the device generates a current which passes from one electrode through the patient's skin to the other electrode thereby mitigating pain.

23 Claims, 9 Drawing Sheets

HEALING DISC, A PAIN MANAGEMENT ASSEMBLY INCORPORATING THE DISC, AND A METHOD OF USING THE SAME

BACKGROUND OF THE INVENTION

1. Technical Field

This invention relates generally to medical devices. More particularly, this invention relates to devices used to mitigate or control pain and promote healing. In particular, the invention relates to a device for delivering a low frequency, low voltage electrical charge to a patient's skin, which device comprises a portable, self-contained unit with built-in electrodes which is engaged in a mounting assembly and worn adjacent the patient's skin so that it is suitably positioned to deliver the charge thereto.

2. Background Information

Transcutaneous electrical neural stimulation (TENS) devices help manage pain utilizing electrical charge. TENS devices utilize FDA approved approaches to manage and relieve pain by cutting off pain signals before they have time to reach the brain. This form of pain management is also believed to release natural pain-fighting endorphins. A TENS device may be worn all day or on an as-needed basis, dependent upon what route the patient and their physician may choose to take.

There are many TENS units on the market today such as the EV807 which is accessible at the website http://mywellcare.ca/tens_units/ev-807p_digital_tens_ems_n.m.e.s These units are typically utilized by physical therapists to help patients recover from injuries. All of these units tend to work in substantially the same way and come with one or two channels. Each channel has two electrodes connected to the main unit by means of wires. The electrodes have a sticky-pad which is adhered to the patient's skin. The electrodes get placed on the patient's skin some distance apart from each other so that the current generated by the main unit of the device is able to flow through the body tissue.

Presently known devices, while they work well, have a downfall in that their wires and their bulk are not ideal for daily use if the patient is actively mobile. Additionally, many of these devices are fairly complex, making them more difficult for some patients to use by themselves.

There is therefore a need in the art for an improved device that is suitable for patients to utilize themselves in order to help manage their pain and help speed recovery from injury.

SUMMARY

A portable, wearable device for managing pain and promoting healing, a pain management assembly including such a device, and a method of using the same is disclosed. The device is a small and completely self-contained device including a housing defining a cavity; a microprocessor situated within the cavity; a power source operatively connected with the microprocessor; and a pair of electrodes. The electrodes comprise two spaced-apart metal contact plates which are mounted in apertures in a bottom wall of the housing. At least a portion of each contact plate extends for a distance outwardly beyond the housing's bottom wall. An electrical charge is delivered to the contact plates which thereby effectively become electrodes which deliver the charge to a patient's skin. The size of the device and lack of wires extending outwardly from its housing make the device easier for a patient to use themselves than was the case with previously known devices.

One or more mounting assemblies are used with the device to provide a management assembly. The mounting assembly may be a strap having a retaining ring into which the device fits, or an adhesive patch configured to receive the device. This renders the device fully portable and enables the patient to be reasonably active while wearing the device and simultaneously receiving treatment therewith. The device is engaged with the mounting assembly and then positioned adjacent the patient's skin. When activated, the device generates a current which passes from one electrode through the patient's skin to the other electrode thereby mitigating pain.

The device is thus more capable of being used discretely by a patient than was the case with previously known TENS devices. Additionally, since the present device does not require wires that connect the device to remotely placed electrodes, the present device is less prone to damage during use and easy to position on the body. The pain management assembly preferably is provided in a kit that includes the device itself with a variety of different mounting assemblies. The enables the patient to select the most appropriate mounting assembly for the region of the body to which they wish to apply the electrical charge. Thus, for a example, the kit may include the device, a strap type mounting assembly for securing the device to an arm or leg, and a variety of differently configured adhesive patches which can be selected based on the part of the body to which they need to be adhered.

The disclosed device, which is a small, compact, portable and self-contained transcutaneous electrical neural stimulation (TENS) device operates at a much lower voltage than previously known device—preferably from about 20V to 25V and delivers around 900 $\mu A$ (900 micro amps) of current. A typical previously known TENS unit operates at a voltage of up to 50 volts, i.e., about twice as much voltage as the present device; and delivers around 100 mA (100 milliamps) of current, i.e., about one hundred times more amps than the present device.

The earth's electromagnetic field generates frequencies of around 10 Hz. Humans exhibit ALPHA brainwaves between 7 and 12 Hz. It has been postulated that the body heals better if it is subjected to frequencies that are in the same frequency range as the earth's electromagnetic field and those of human brain waves. The present device is configured so that it will generate frequencies in this desired range. This is unlike previously known TENS units Because the present device is so portable, it can be worn daily, so the device's beneficial effects to tissues are able to take place over a period of time.

In one aspect, the invention may provide a device for managing pain and promoting healing, said device comprising:
 a housing;
 a cavity defined in the housing;
 a microprocessor provided within the housing's cavity;
 a power source operatively connected with the microprocessor; and
 a pair of electrodes mounted on the housing and being operatively connected with the microprocessor and the power source; said electrodes being configured to deliver a charge to a patient's skin.

In another aspect, the invention may provide a pain management and healing assembly comprising:
 a device including:
 a housing;
 a cavity defined in the housing;
 a microprocessor provided within the housing's cavity;

a power source operatively connected with the microprocessor; and a pair of electrodes mounted directly on the housing and being operatively connected with the microprocessor and the power source; and a mounting assembly configured to engage the device and retain the device adjacent a patient's skin; and wherein the device is operable to cause current from the electrodes to flow through the patient's skin.

In yet another aspect, the invention may provide a method of relieving pain and promoting healing; said method including the steps of:

providing a portable transcutaneous electrical neural stimulation (TENS) device having a housing; a cavity defined in the housing; a microprocessor provided within the housing's cavity; a power source operatively connected with the microprocessor; and a pair of electrodes mounted directly on the housing and being operatively connected with the microprocessor and the power source; and engaging the TENS device in a mounting assembly;

positioning the TENS device adjacent the patient skin and retaining the same there against by means of the mounting assembly; and generating a current through the patient's skin using the electrodes.

BRIEF DESCRIPTION OF THE SEVERAL VIEWS OF THE DRAWINGS

A sample embodiment of the invention, illustrative of the best mode in which Applicant contemplates applying the principles, is set forth in the following description, is shown in the drawings and is particularly and distinctly pointed out and set forth in the appended claims.

Similar numbers refer to similar parts throughout the drawings.

DETAILED DESCRIPTION

Figure 1:
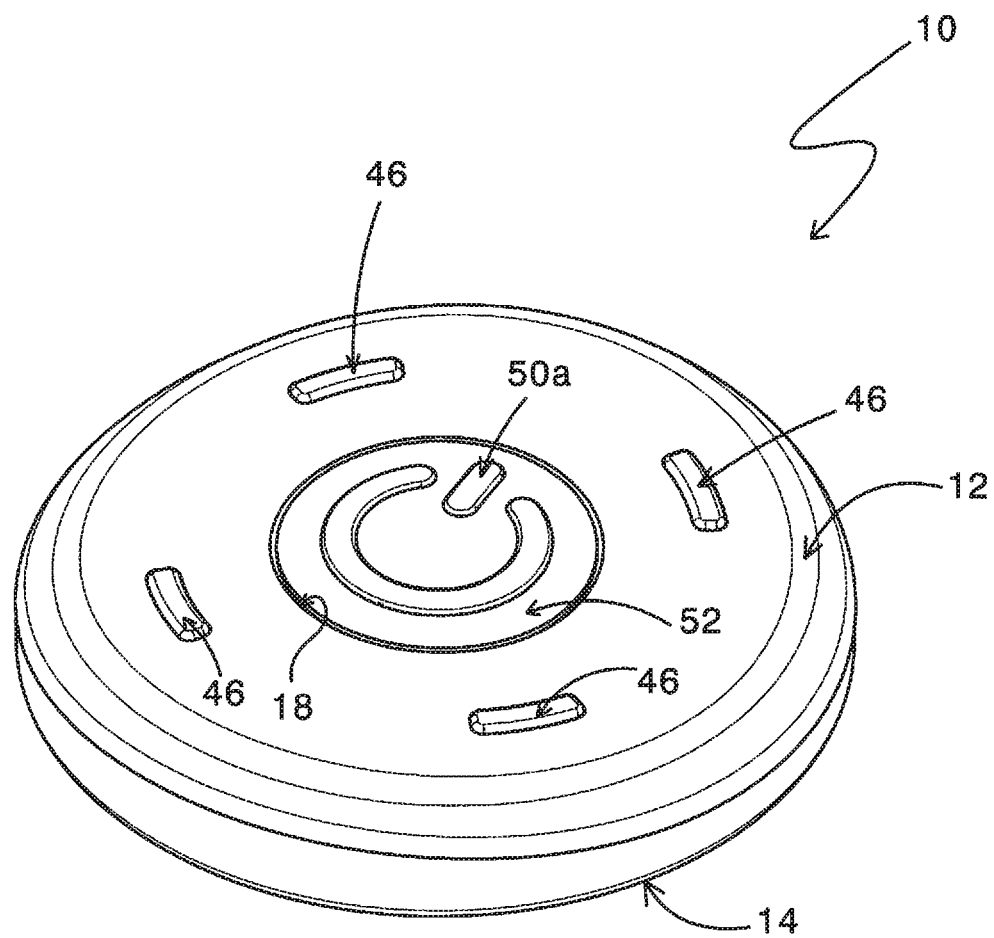
FIG. 1 is a perspective view of a healing disc in accordance with an aspect of the present invention.

Referring to FIGS. 1-12 there is shown a healing disc or device in accordance with an aspect of the present invention, generally indicated at 10.

Disc 10 includes an upper housing 12 and a lower housing 14 which are configured to matingly engage each other and define an interior cavity (not shown but formed between the upper and lower housing's interior surfaces). Various components are housed within this cavity, as will be described hereafter.

Upper and lower housings 12, 14 preferably are fabricated from polycarbonate plastic, although any other suitable materials may be used instead. Upper housing 12 is gently curved toward its outer edge (as shown at 12b in FIG. 5) so that disc 10 does not present any sharp edges which may injure the patient. Upper and lower housings 12, 14 together form a unit that is generally circular in shape when viewed from the top or bottom and is relatively thin. Disc 10 preferably has a diameter of approximately 1½ inches and the overall thickness of disc 10 is about 3/62 inch.

Upper housing 12 has an exterior surface 12a and an interior surface (not shown). A generally circular central aperture 18 is defined in upper housing 12 and extends between the exterior and interior surfaces thereof. Upper housing 12 further defines four generally rectangular slots 20 which are spaced outwardly from aperture 18 and are preferably equidistant from each other. Slots 20 extend between the exterior and interior surfaces of upper housing 12 and are arranged to circumscribe aperture 18. Any other configuration of aperture 18 and slots 20 may be utilized.

Lower housing 14 has an exterior surface 14a and an interior surface 14b. A pair of spaced-apart apertures 22 is defined in a bottom wall 14c of lower housing 14. Apertures 22 extend between the exterior and interior surfaces 14a, 14b of lower housing 14 and preferably are generally semi-circular in shape. A hole 24 is defined in a side region of lower housing 14 and extends between the exterior and interior surfaces 14a, 14b. A pair of posts 26 extends upwardly from the interior surface of bottom wall 14c. Posts 26 and disposed generally at right angles to bottom wall 14c and extend toward upper housing 12 when upper and lower housings 12, 14 are engaged with each other. Disc 10 further includes a pair of contact plates 32, which are complementary in shape and size to apertures 22 in lower housing 14. Contact plates 32 are engaged in apertures 22 so that they project for a slight distance outwardly beyond the exterior surface of bottom wall 14c of lower housing 14. This ensures that plates 32 will contact the patient's skin when disc 10 is worn on the body, as will be described later herein. Contact plates 32 are electrodes that will pass a current to the patient's skin in order to block pain. Contact plates 32 preferably are fabricated from metal. In previously known TENS units, the electrodes are connected via wires to components within the housing and those wires extend for a distance outside of the unit's housing. Disc 10 is differently configured in that electrodes 32 are mounted directly to housing 12/14 and disc 10 is free of any wires which extend outwardly from the housing.

A printed circuit board (PCB) 36 is provided within the housing formed by upper and lower housing 12, 14. PCB 36 is planar and generally circular in shape, and defines a pair of holes 38 therein and through which posts 26 extend to retain PCB 36 in place. PCB 36 is operatively connected with contact plates 32 via conductive springs 40. A USB charger 42 extends through hole 24 in lower housing 14 and is operatively connected with PCB 36.

Figure 5:
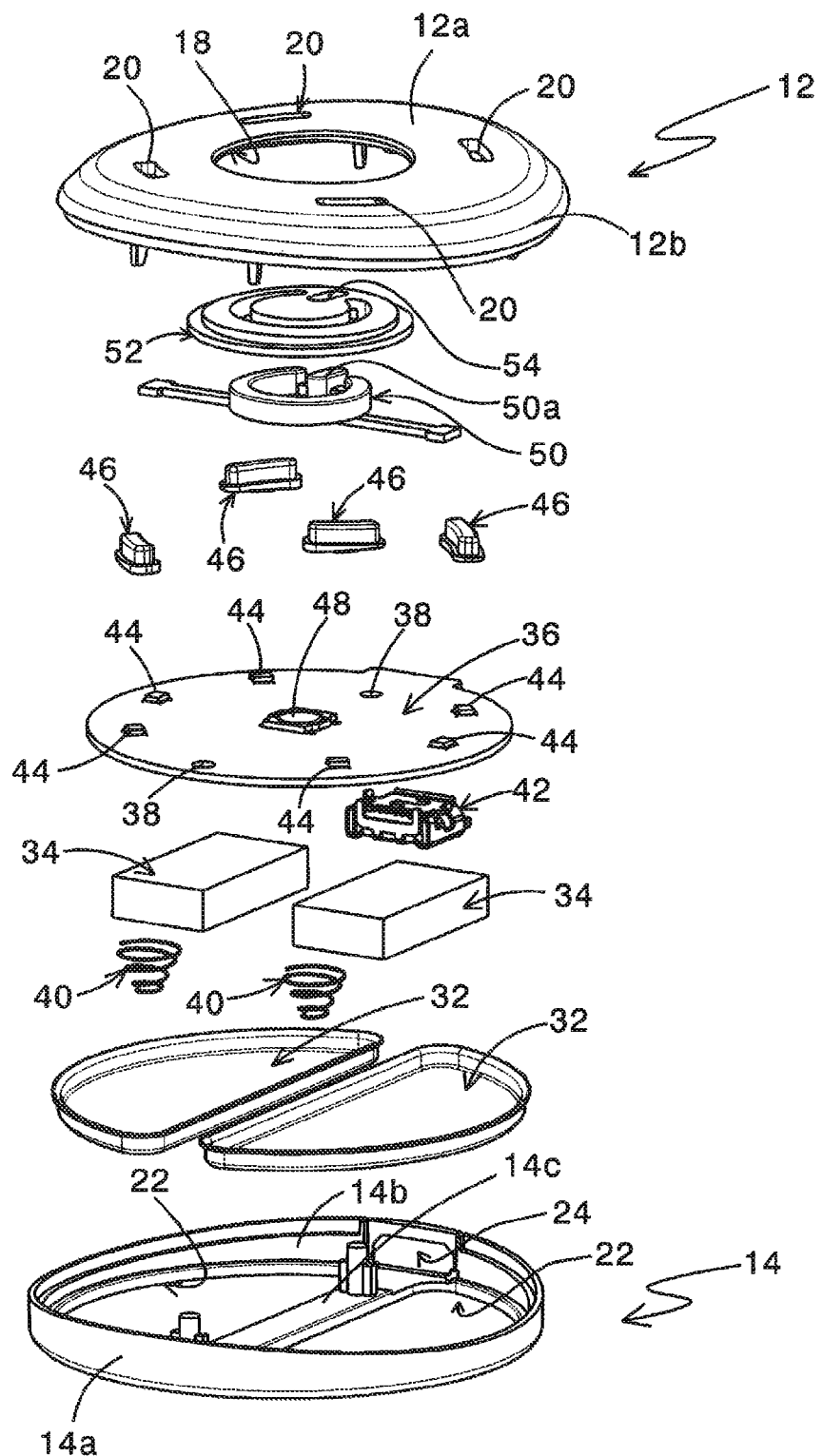
FIG. 5 is an exploded perspective view of the healing disc.

A power source is also provided within disc 10. As shown in FIG. 5, this power source comprises two rechargeable batteries 34, each of which fits inside a recessed region of one of contact plates 32. Batteries 34 are operatively connected to all components within disc 10 that require power.

Although not illustrated herein, it will be understood that batteries 34 may be recharged by plugging a cord into a wall transformer or into a USB port. FIG. 5 shows disc 10 including USB charger 42 which will permit disc 10 to be recharged by plugging it into a computer. Batteries 34 are sized so that together they will provide an output voltage of from about 20V to about 25V and an amperage of about 900 micro amps or less. Disc 10 is able to selectively generate current at four different frequencies, namely, about 4 Hz, 6.8 Hz, 7.83 Hz, and 11 Hz. It will be understood that only one battery could be utilized in disc 10 or more than two batteries could be utilized therein. Furthermore, any other suitable power source may be used instead of batteries 34.

Figure 2:
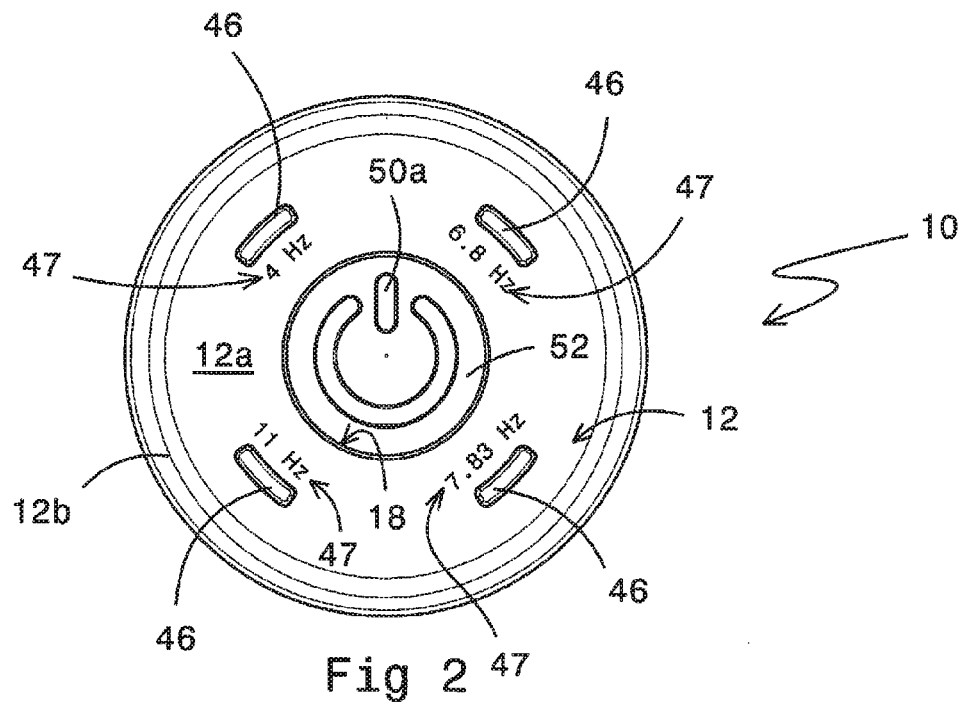
FIG. 2 is a top view of the healing disc.
Figure 3:
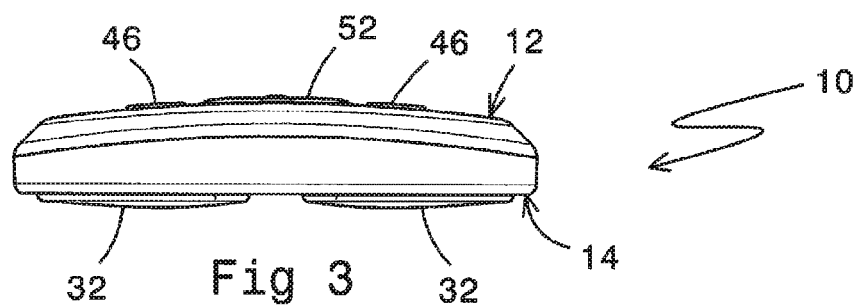
FIG. 3 is a side view of the healing disc.
Figure 4:
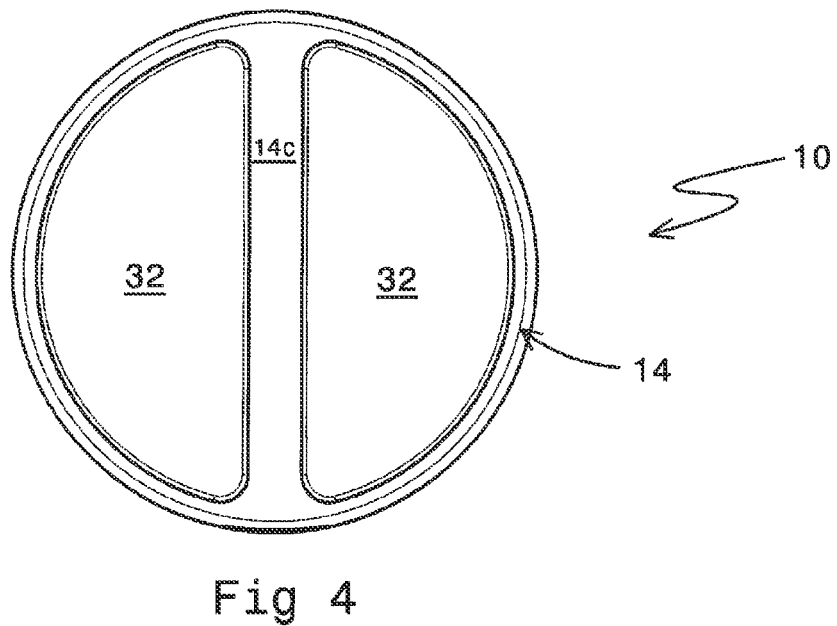
FIG. 4 is a bottom view of the healing disc.

PCB 36 also includes a plurality of LEDs 44. Disc 10 further includes four indicator lightpipes 46, each of which being shaped and sized so that a portion thereof is received through one of slots 20 in upper housing 12. Each indicator lightpipe 46 is positioned to be disposed over one of LEDs 44. Each LED 44 positioned adjacent one of the indicator lightpipes 46 is able to be activated to indicate the one of four output frequencies that is being generated by device. As shown in FIG. 2, upper housing 12 preferably includes an indicator 47 are associated with each lightpipe 46. Indicators 47 identify the frequency being outputted by disc 10 when the associated lightpipe 46 is illuminated. The indicators 47 may take any form. FIG. 2 illustrates numerical markings placed on exterior surface 12a of upper housing 12. Alternatively, indicators 47 may be digital readouts displayed on a screen window provided on upper housing 12.

A button switch 48 is provided centrally on PCB 36 and a button lightpipe 50 is disposed over button switch 48 and over two LEDs 44. A button bezel 52 is disposed over button lightpipe 50. Bezel 52 is shaped and sized so that a portion thereof extends through aperture 18 in upper housing 12. Bezel 52 defines a slot 54 therein. A portion 50a of button lightpipe 50 extends through slot 54 in bezel 52. Bezel 52 preferably is fabricated from an elastomer. Bezel 52 is engaged with button switch 48. When depressed, button switch 48 will switch the device on or off and portion 50a of button lightpipe 50 will light up (if the device is on) or will cease to be illuminated (if the device is switched off).

PCB 36 includes a microprocessor and other electronics similar to a TENS device. Microprocessor includes programming which will control the operation of disc 10. In particular, the programming controls the charge outputted by contact plates 32 and controls the timing and duration of that output. Preferably, the microprocessor activates contact plates 32 for repeating cycles of 15 seconds on followed by 5 seconds off, i.e., 15 seconds of delivering a charge to the patient's skin followed by 5 seconds of no charge being delivered to the patient's skin. This on/off cycle is repeated for a pre-determined time period, preferably 20 minutes and then disc 10 shuts off automatically.

As indicated previously, button switch 48 is used to switch disc on and off. The patient will depress bezel 52 and hold for 2 seconds to step through four standard pre-set frequencies. When the desired frequency is indicated by the illumination of the LED 44 adjacent the indicator 47 which represents that desired frequency, the patient will stop depressing bezel 52. Disc 10 will then generate the frequency indicated by the illuminated LED 44 for the 20 minute cycle and will then shut off automatically. When the patient next switches disc 10 on, the previously set frequency is remembered and the device will operate at that frequency. If the patient wishes to change the frequency, they will continue to hold down the button switch 48 to cause the device to step through the pre-set frequencies as previously described and will stop depressing switch 48 when the desired frequency is reached (i.e., when the LED 44 adjacent the appropriate indicator 47 is illuminated).

Figure 6:
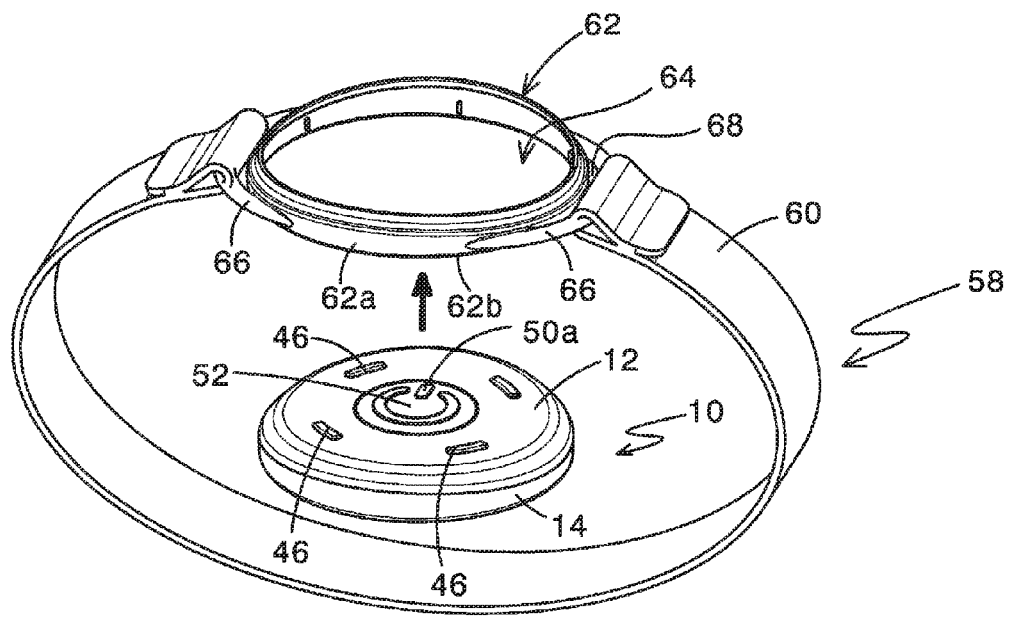
FIG. 6 is a perspective view of a first mounting assembly showing the healing disc separated therefrom and ready for insertion into the assembly.
Figure 7:
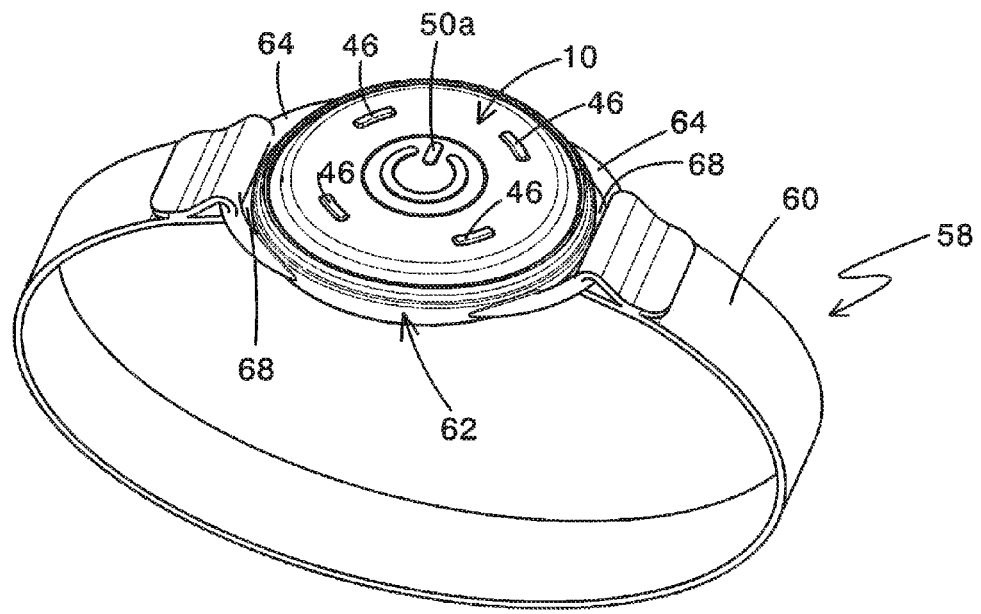
FIG. 7 is a perspective top view of the first mounting assembly with the healing disc engaged therewith.
Figure 8:
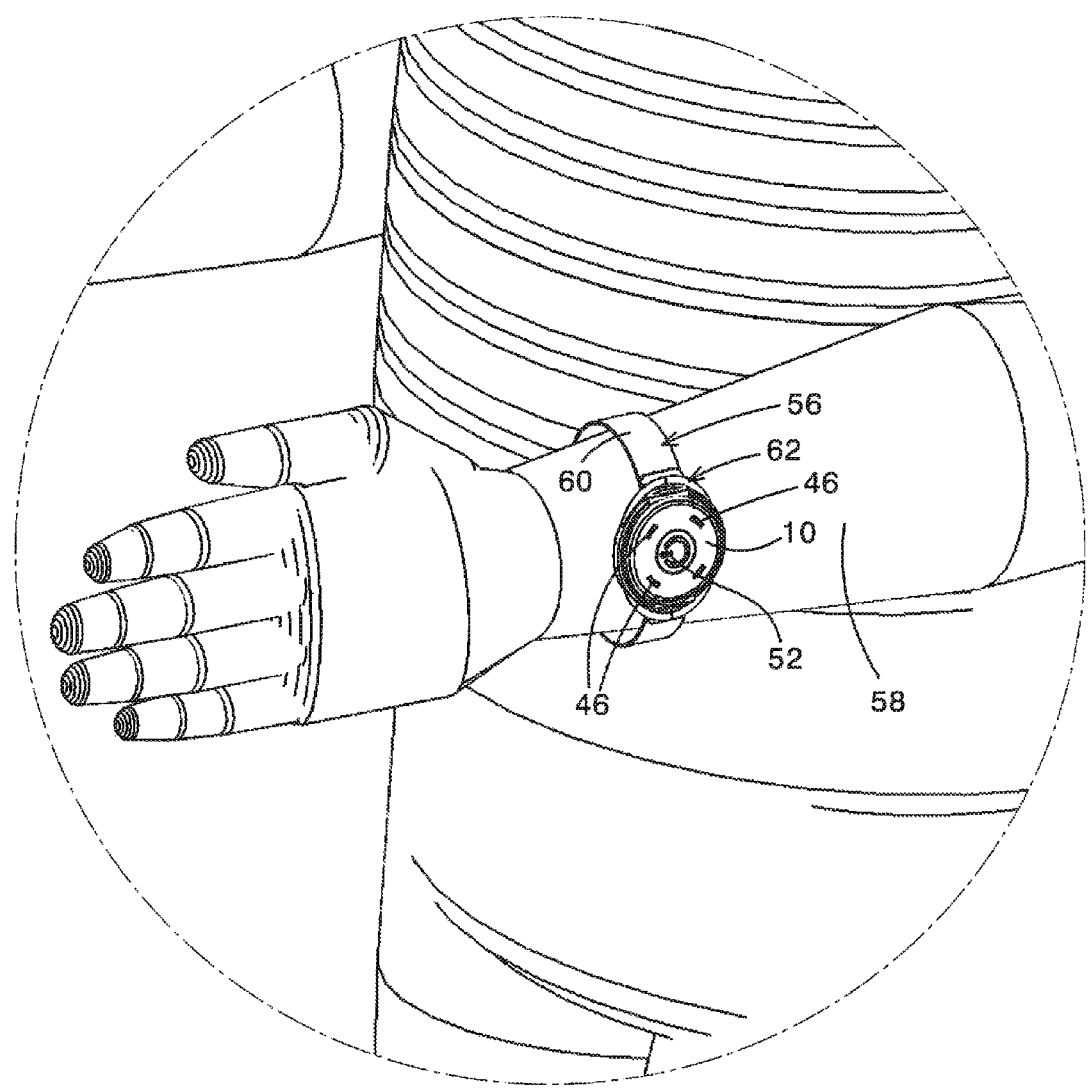
FIG. 8 is a perspective view showing the first mounting assembly with the healing disc engaged therewith worn on a patient's arm.

Disc 10 is configured to be worn adjacent the patient's skin. FIGS. 6 through 12 show various ways in which disc 10 can be retained adjacent a patient's skin. FIGS. 6-8 show a first pain management assembly which comprises a first mounting assembly and the disc 10. This first mounting assembly is a holder 58 which is configured to wrap around and be secured to a patient's arm 58 or leg (not shown). Holder 56 includes a strap 60 configured to encircle the arm 58 or leg. Strap 60 may be fabricated from an elastic type material so that it can be stretched in order to place it on the patient's arm or leg. Alternatively, strap 60 may be fabricated from a non-elastic material and be provided with a locking mechanism (not shown) which is operable to secure strap 60 to arm 58 (or leg). Holder 56 further includes a retainer ring 62. Retaining ring 62 includes a peripheral wall 62a which bounds and defines a central aperture 64. Aperture 64 is slightly larger in diameter than the exterior diameter of lower housing 14. A lip (not numbered) formed on the upper edge of retainer ring 62 bounds aperture 64 and is provided to keep disc 10 retained therein, as will be further described. A pair of C-shaped flanges 66 extends outwardly from peripheral wall 62a and each flange 66 is disposed generally at right angles to wall 62a. An slot 68 is defined between each flange 66 and peripheral wall 62a of retaining ring 62. Each end of strap 60 is threaded through one of slots 68 and is secured back upon itself. Disc 10 is inserted into holder 56 from the bottom as indicated by the arrow shown in FIG. 6. Disc 10 snap-fits into retainer ring 62 and is retained therein by frictional contact with the interior surface of wall 62a and by the lip which bounds aperture 64. Although not numbered, it can be seen that several ridges are provided on the interior surface of wall 62a to aid in frictionally retaining disc 10 therein. When disc 10 is retained in ring 62, the bottom wall 14c of lower housing 14 is positioned so that contact plates 32 will project beyond a lower edge 62b of ring 62 so that plates 32 are able to contact the patient's skin. Strap 60 is placed around the patient's arm 58 and is moved along the arm to the position adjacent where the patient is experiencing pain. The patient will then depress bezel 52 to activate switch 48 and switch disc 10 on, holding bezel 52 down to select the desired frequency, and then disc 10 will generate current and deliver a charge to the skin below disc 10 via electrodes 32 as has been previously described. When disc 10 switches off automatically, the patient may continue to wear the assembly until they next wish to administer another treatment. If the patient wishes to remove disc 10 from holder 58 they will remove strap 60 from their arm and simply apply pressure to the upper surface 12a of upper housing 12 and push disc 10 out of retaining ring 62.

Figure 9:
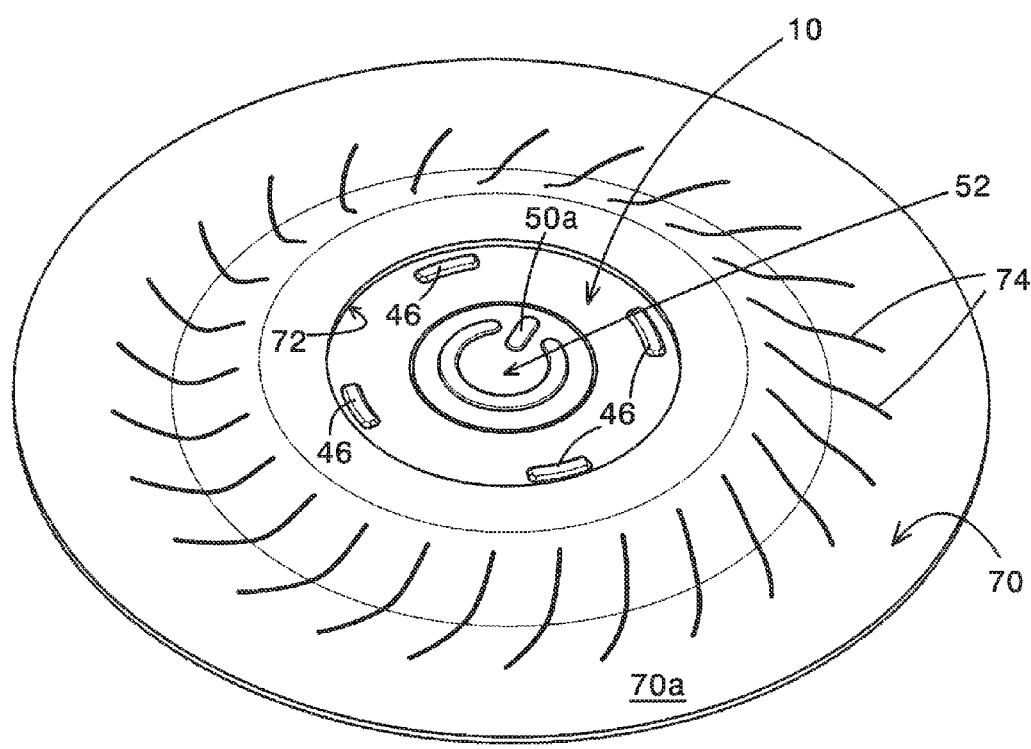
FIG. 9 is a perspective top view of a second mounting assembly with the healing disc engaged therewith.
Figure 10:
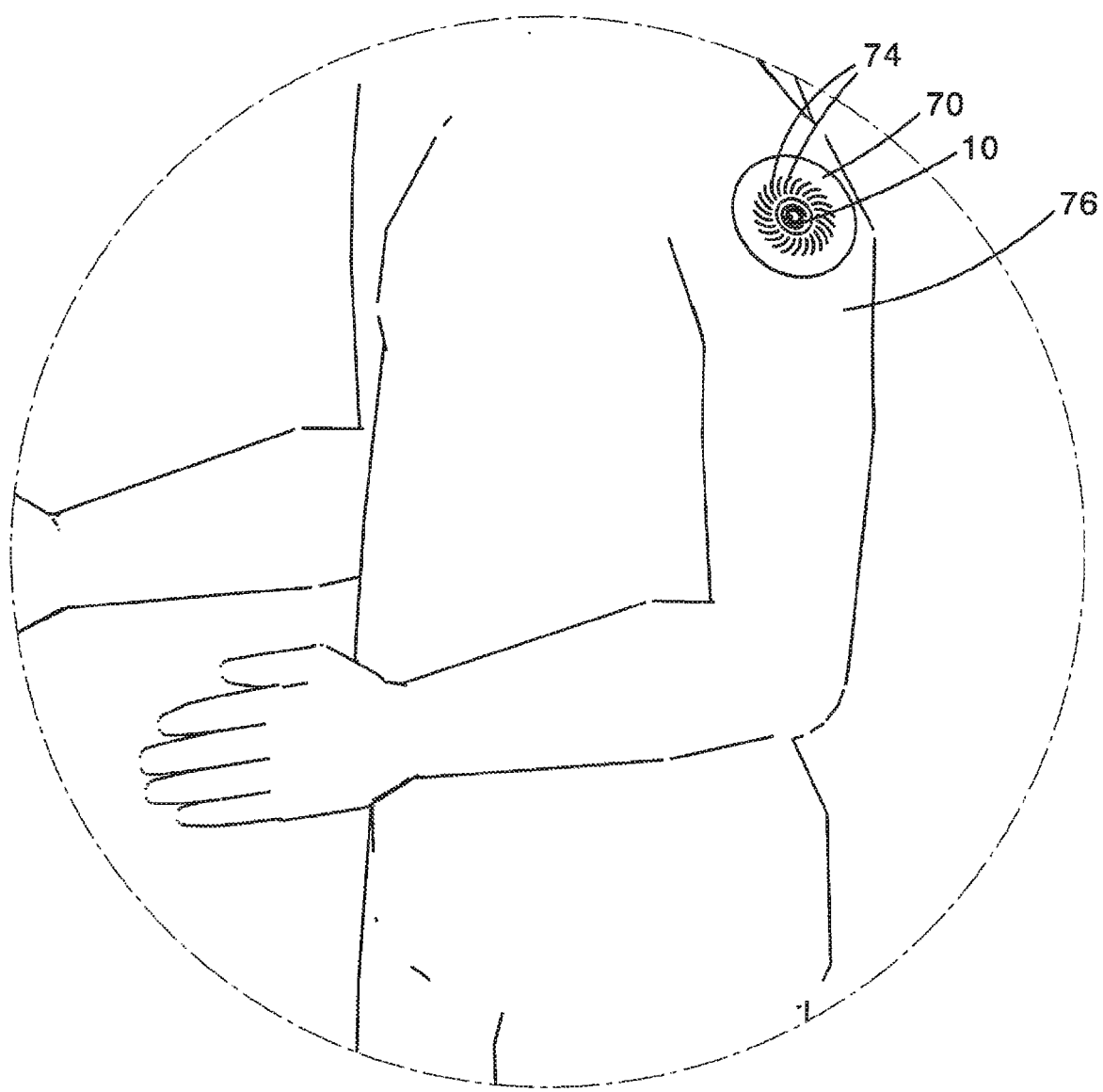
FIG. 10 is a perspective view showing the second mounting assembly with the healing disc engaged therewith being worn on a patient's arm.

FIGS. 9 and 10 show a second pain management assembly in accordance with an aspect of the invention. This second pain management assembly includes a second mounting assembly and the disc 10. The second mounting assembly comprises an adhesive patch 70 which is configured to engage and retain disc 10 adjacent the patient's skin. Patch 70 is generally circular and includes an upper surface 70 and a lower surface (not shown). An adhesive layer is applied to the lower surface of patch 70. A central aperture 72 is defined in patch 70 and is dimensioned so that it is slightly smaller than the exterior diameter of disc 10. When disc 10 is engaged in patch 70, a portion of the lower surface of patch 70 contacts an upper exterior surface 12a of upper housing 12 of disc 10 and the adhesive layer on the lower surface of patch 70 adheres disc 10 to patch 70. Patch 70 extends for a distance outwardly beyond disc 10 and this additional portion of patch 70 is placed in contact with the patient's skin and adheres thereto.

Figure 11:
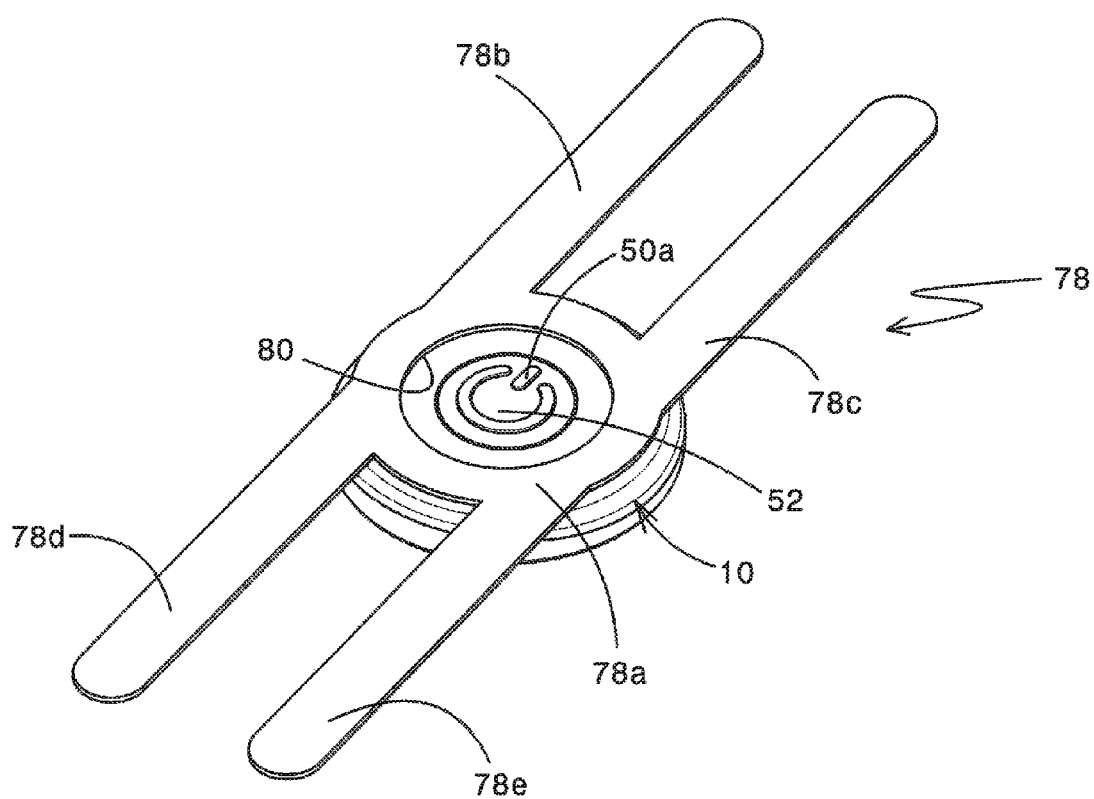
FIG. 11 is a perspective top view of a third mounting assembly with the healing disc engaged therewith.

Patch 70 preferably includes a plurality of slits 74 which are spaced a distance outwardly of aperture 72. Slits 74 extend radially outwardly away from aperture 72 and are spaced apart from each other. Slits 74 are provided so that patch 70 is able to conform to the shape of the part of the body to which the patient wishes to apply patch 70. This configuration of patch 70 enables the patient to position the disc 10 adjacent almost any injured part of the body. FIG. 11 illustrates patch 70 with disc 10 engaged therewith adhesively secured to the upper region of a patient's arm 76.

Figure 12:
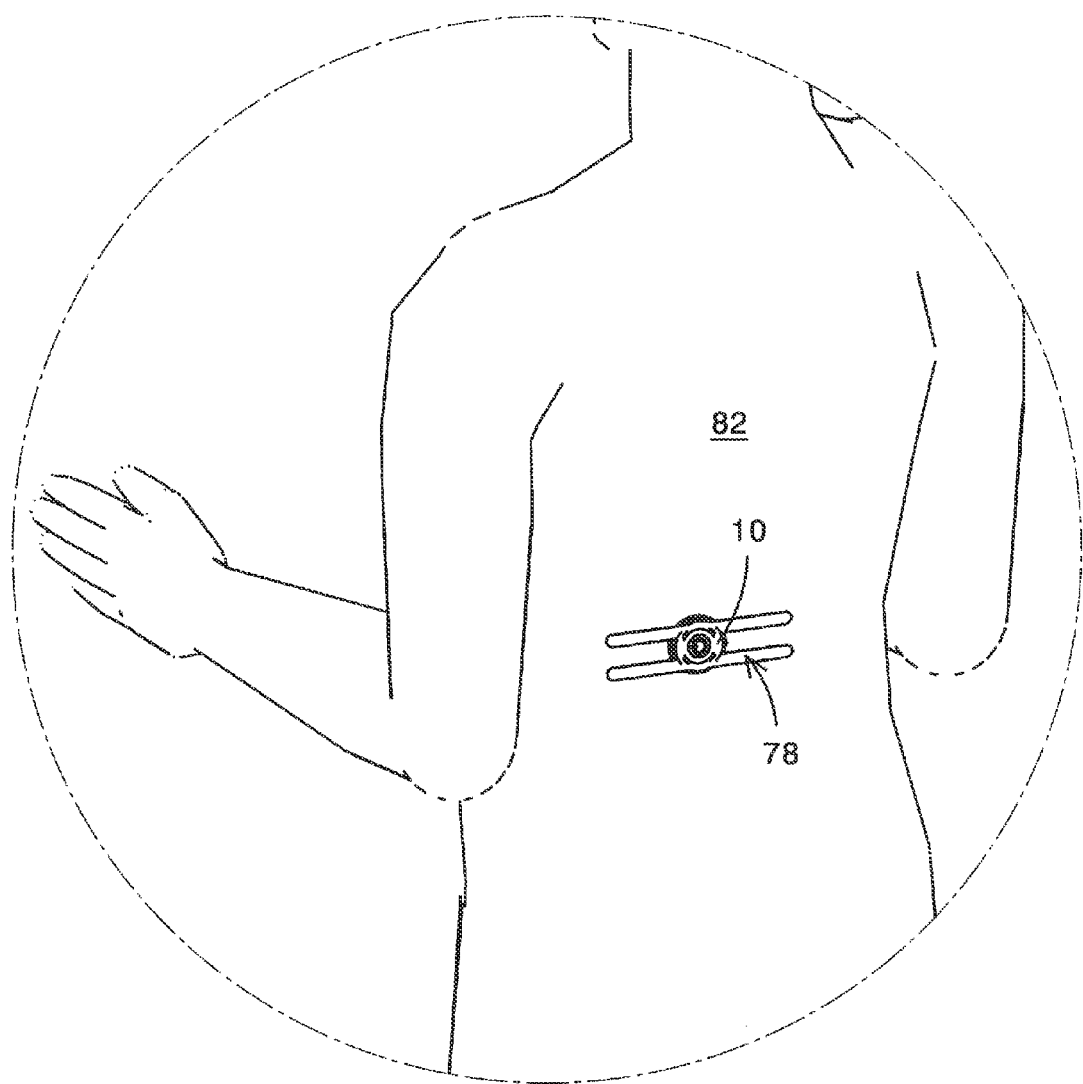
FIG. 12 is a perspective view of the third mounting assembly with the healing disc engaged therewith being worn on a patient's back.

FIGS. 11 and 12 show a third pain management assembly comprising a third embodiment of a mounting assembly which is able to engage disc 10 and to retain the same adjacent a patient's skin. The third embodiment of the mounting assembly comprises an adhesive patch 78. Patch 78 is generally H-shaped and includes a central region 78a from which extend outwardly pairs of legs 78b, 78c, 78d, and 78e. Preferably, central region 78a is generally circular in shape and defines an aperture 80 therein. Aperture 80 extends between an exterior surface and an interior surface of patch 78 and is sized to be just slightly smaller in diameter than disc 10. An adhesive layer (not shown) is applied to interior surface of central region 78a and to the interior surfaces of legs 78b, 78c, 78d, and 78e. Thus, a portion of patch 78 overlays portion of the exterior surface of upper housing 12 of disc 10 and the adhesive layer disposed between patch 78 and disc 10 keeps disc 10 engaged with patch 78. The adhesive layer on the legs 78b, 78c, 78d, and 78e retain the disc 10 on the patient's skin. FIG. 12 shows patch 78 being utilized to secure disc 10 to a patient's back 82.

It will be understood that with both patch 70 and patch 78 the adhesive regions thereof are preferably initially covered with a non-adhesive protective layer that is peeled off immediately prior to use. Patches 70 and 78 are used in much the same manner as an adhesive plaster. If patch 70 or 78 is to be applied in a region of the patient's body that is easily accessed once applied, disc 10 may be activated (as previously described) after application of the patch. If, patch 70 or 78 is to be applied in a region of the patient's body that will not be easily accessed after application of the patch, then disc 10 is activated prior to application of the patch on the body. Once the patient is finished treatment, the adhesive patch 70 or 78 is simply pulled off the skin and disposed of.

It will be understood that disc 10 could be supplied in a kit which includes the first mounting assembly 58 and one or both of the second mounting assembly 70 and third mounting assembly 78. This kit would enable a patient to select which mounting assembly is most appropriate for using for treatment of a particular region of their body. The kit may include additional or other differently configured mounting assemblies which will enable the patient to wear disc 10 adjacent their skin.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the invention are an example and the invention is not limited to the exact details shown or described.

The invention claimed is:

1. A device for managing pain and promoting healing, said device comprising:
    a housing placeable on a patient's skin;
    a programmable microprocessor provided with the housing;
    a power source operatively connected with the microprocessor; and
    a pair of electrodes projecting outwardly from the housing; wherein programming within the microprocessor activates and controls the generation and delivery of a current through the electrodes to the patient's skin for a total period of time comprising a treatment session; wherein the programming generates and delivers a current of about 900 µA or less at a pre-set frequency of about 11 Hz or less for substantially all of the treatment session; and wherein the programming causes the device to operate at a voltage of from about 20V to about 25V.

2. The device as defined in claim 1, wherein the housing has a bottom wall adapted to be disposed adjacent a patient's skin; and a pair of spaced-apart apertures are defined in the bottom wall; and wherein the electrodes are mounted on the housing so that each electrode extends at least partially through one of the apertures.

3. The device as defined in claim 2, wherein each electrode comprises a metallic contact plate.

4. The device as defined in claim 1, wherein the electrodes extend outwardly for a distance beyond a bottom wall of the housing.

5. The device as defined in claim 1, wherein the device is free of any wires that extend outside of the housing.

6. The device as defined in claim 1, wherein the programming causes current to be generated at a first pre-set frequency of about 4 Hz; or at a second pre-set frequency of about 6.8 Hz; or at a third pre-set frequency of about 7.83 Hz; or at a fourth pre-set frequency of about 11 Hz.

7. The device as defined in claim 1, wherein the programming controls a preset pattern of on-off cycles for the electrodes which pattern is followed for preset periods of treatment time.

8. The device as defined in claim 7, wherein the preset pattern includes 20 seconds on, 5 seconds off for a total of 20 minutes of time per treatment session.

9. The device as defined in claim 1, wherein the housing has a diameter of about 1½ inches and is about 3/16 inch thick.

10. The device as defined in claim 1, wherein the housing is portable and is adapted to be worn by the patient.

11. The device as defined in claim 1, wherein the power source is rechargeable.

12. A pain management and healing assembly comprising:
    a housing;
    a cavity defined in the housing;
    a microprocessor provided within the cavity;
    a power source provided within the cavity and operatively connected with the microprocessor;
    a pair of electrodes mounted on the housing and being operatively connected with the microprocessor and the power source; and
    a mounting assembly configured to engage the housing and retain the housing adjacent a patient's skin; wherein the device is operable to cause a current of about 900 µA to flow from the electrodes and through the patient's skin; wherein the device operates at a voltage of from about 20V up to about 25V; wherein the electrodes generate electricity at one of a plurality of pre-set substantially constant frequencies ranging from about 4 Hz up to about 11 Hz; and wherein the current and the pre-set frequencies are maintained for substantially an entire treatment session; and wherein the mounting assembly comprises:

a strap adapted to encircle a limb of the patient;

a retaining ring provided on the strap; and a recess defined in the base and shaped complementary to at least a portion of the device; and wherein the portion of the device is received in the recess and is retained therein in such a manner that the electrodes are positioned to contact the patient's skin when the strap encircles the limb of the patient.

13. A pain management and healing assembly comprising:
a housing;
a cavity defined in the housing;
a microprocessor provided within the cavity;
a power source provided within the cavity and operatively connected with the microprocessor;
a pair of electrodes mounted on the housing and being operatively connected with the microprocessor and the power source; and
a mounting assembly configured to engage the housing and retain the housing adjacent a patient's skin; wherein the device is operable to cause a current of about 900 µA to flow from the electrodes and through the patient's skin; wherein the device operates at a voltage of from about 20V up to about 25V; wherein the electrodes generate electricity at one of a plurality of pre-set substantially constant frequencies ranging from about 4 Hz up to about 11 Hz; and wherein the current and the pre-set frequencies are maintained for substantially an entire treatment session; and wherein the mounting assembly comprises:
an adhesive patch, wherein said adhesive patch has a diameter that is greater than an external diameter of the device;
an aperture defined in the adhesive patch; said aperture having a diameter that is less than the external diameter of the device; and wherein the adhesive patch is engaged with the device such that a part of an upper surface of the device is accessible through the aperture and the adhesive patch overlaps the remaining portion of the upper surface of the device; and wherein the patch is adapted to be adhered to the patient's skin in such a manner that the electrodes on a bottom wall of the device are brought into contact with the patient's skin.

14. The pain management assembly as defined in claim 13, wherein the adhesive patch is generally circular in shape and includes a plurality of slits disposed a distance annularly outwardly from the aperture.

15. The pain management assembly as defined in claim 14, wherein the slits radiate outwardly away from the aperture and are spaced a distance apart from each other.

16. The pain management assembly as defined in claim 14, wherein the slits are disposed in a circle that is concentric with the aperture.

17. The pain management assembly as defined in claim 13, wherein the patch is generally H-shaped and includes two pairs of legs extending outwardly from opposite portions of a central region which defines the aperture therein through which the upper face of the device is accessible, and wherein the legs of each pair of legs are disposed generally parallel to each other and spaced laterally apart from each other.

18. The pain management assembly as defined in claim 12, further comprising a second mounting assembly usable instead of the mounting assembly; and wherein the second mounting assembly includes:
a first adhesive patch, wherein said adhesive patch has a diameter that is greater than an external diameter of the device;
an aperture defined in the adhesive patch; said aperture having a diameter that is less than the external diameter of the device; and wherein the adhesive patch is selective engaged with the device instead of the strap such that a part of an upper surface of the device is accessible through the aperture and the adhesive patch overlaps the remaining portion of the upper surface of the device; and wherein the patch is adapted to be adhered to the patient's skin in such a manner that the electrodes on a bottom wall of the device are brought into contact with the patient's skin.

19. The pain management assembly as defined in claim 18, further comprising a third mounting assembly usable instead of either of the first and second assemblies; and wherein the third mounting assembly comprises a generally H-shaped adhesive patch which includes a central region with two pairs of legs extending outwardly from opposite portions of the central region; an aperture defined in the central region and through which the upper face of the device is accessible, and wherein the legs of each pair of legs are disposed generally parallel to each other and spaced laterally apart from each other.

20. A method of relieving pain and promoting healing; said method including the steps of:
providing a device for managing pain and promoting healing as defined in claim 8;
positioning the device against the patient's skin;
generating a current through the patient's skin using the electrodes where the current is at about 900 µA or less and is generated at a frequency of less than about 11 Hz; and
maintaining the current and frequency for substantially an entire treatment session.

21. The method as defined in claim 20 wherein the step of generating the current includes generating the current at one of a plurality of pre-set frequencies where the pre-set frequencies range from about 4 Hz to about 11 Hz.

22. The method as defined in claim 20, wherein the step of operating the device includes operating the device at the voltage of from about 20V to about 25V.

23. The method as defined in claim 20, further comprising the steps of:
engaging the device in a mounting assembly; and
retaining the device against the patient's skin by means of the mounting assembly.

* * * * *

UNITED STATES PATENT AND TRADEMARK OFFICE
CERTIFICATE OF CORRECTION

| | | |
|---|---|---|
| PATENT NO. | : 9,433,785 B2 | |
| APPLICATION NO. | : 14/058405 | |
| DATED | : September 6, 2016 | |
| INVENTOR(S) | : Garth Howard Holding et al. | |

It is certified that error appears in the above-identified patent and that said Letters Patent is hereby corrected as shown below:

In the claims,

Column 10, line 40 (Claim 20) "claim 8" should be changed to --claim 1--.

Signed and Sealed this
Twenty-ninth Day of November, 2016

Michelle K. Lee
*Director of the United States Patent and Trademark Office*